US012642177B2

(12) United States Patent
Meyers et al.

(10) Patent No.: US 12,642,177 B2
(45) **Date of Patent: \*Jun. 2, 2026**

(54) KERNEL-LEVEL GRAIN MONITORING SYSTEMS FOR COMBINE HARVESTERS

(71) Applicant: Deere & Company, Moline, IL (US)

(72) Inventors: Zachary A Meyers, Milan, IL (US); Stephen R. Corban, Geneseo, IL (US); Jeremiah K. Johnson, Williamsburg, IA (US); Alexander B. Lassers, Davenport, IA (US)

(73) Assignee: DEERE & COMPANY, Moline, IL (US)

( \* ) Notice: Subject to any disclaimer, the term of this patent is extended or adjusted under 35 U.S.C. 154(b) by 19 days.

This patent is subject to a terminal disclaimer.

(21) Appl. No.: 18/771,384

(22) Filed: Jul. 12, 2024

(65) Prior Publication Data

US 2024/0357967 A1 Oct. 31, 2024

Related U.S. Application Data

(62) Division of application No. 17/088,042, filed on Nov. 3, 2020, now Pat. No. 12,063,885.

(51) Int. Cl.
*A01D 41/127* (2006.01)
*A01F 12/44* (2006.01)
(Continued)

(52) U.S. Cl.
CPC ..... *A01D 41/1277* (2013.01); *A01D 41/1272* (2013.01); *A01D 41/1273* (2013.01);
(Continued)

(58) Field of Classification Search
CPC .............. A01D 41/1271–1273; A01D 41/1277
See application file for complete search history.

(56) References Cited

U.S. PATENT DOCUMENTS 5,708,366 A 1/1998 Nelson
5,934,997 A 8/1999 Nelson et al.
(Continued)

FOREIGN PATENT DOCUMENTS

CN 105705002 A 6/2016
CN 106198885 A 12/2016
(Continued)

OTHER PUBLICATIONS

Kormann et al., Testing Stand for Yield Measurement Systems in Combine Harvesters, 1998 ASAE Annual International Meeting, Paper No. 983102, Jul. 1988. (10 pages).
(Continued)

*Primary Examiner* — Raphael Schwartz
(74) *Attorney, Agent, or Firm* — KLINTWORTH & ROZENBLAT LLP

(57) ABSTRACT

Embodiments of a kernel-level grain monitoring system include a grain camera positioned to capture bulk grain sample images of a currently-harvested grain taken into and processed by a combine harvester, a moisture sensor, and a display device. A controller architecture is coupled to the grain camera, to the moisture sensor, and to the display device. The controller architecture is configured to: (i) analyze the bulk grain sample images, as received from the grain camera, to determine an average per kernel (APK) volume representing an estimated volume of a single average kernel of the currently-harvested grain; (ii) repeatedly calculate one or more topline harvesting parameters based, at least in part, on the determined APK volume and the moisture sensor data; and (iii) selectively present the topline harvesting parameters on the display device for viewing by an operator of the combine harvester.

20 Claims, 5 Drawing Sheets

(51) Int. Cl.

| | | |
|---|---|---|
| *G01F 1/76* | (2006.01) |
| *G01G 19/08* | (2006.01) |
| *G01N 33/02* | (2006.01) |
| *G06T 7/62* | (2017.01) |
| *H04N 7/18* | (2006.01) |

(52) U.S. Cl.

CPC ........ *A01D 41/1275* (2013.01); *A01F 12/444* (2013.01); *G01F 1/76* (2013.01); *G01G 19/08* (2013.01); *G01N 33/02* (2013.01); *G06T 7/62* (2017.01); *G06T 2207/30188* (2013.01); *H04N 7/18* (2013.01)

(56) References Cited

U.S. PATENT DOCUMENTS

| | | | |
|---|---|---|---|
| 5,970,800 A | 10/1999 | Gunneskov et al. | |
| 6,147,502 A | 11/2000 | Fryer et al. | |
| 6,526,120 B1 | 2/2003 | Gray et al. | |
| 6,606,571 B2 | 8/2003 | Phelan et al. | |
| 9,410,840 B2 | 8/2016 | Acheson et al. | |
| 9,516,817 B2 | 12/2016 | Temple et al. | |
| 9,631,964 B2 | 4/2017 | Gelinske et al. | |
| 9,779,330 B2 | 10/2017 | Wellington et al. | |
| 9,901,031 B2 | 2/2018 | Mott et al. | |
| 10,371,558 B2 | 8/2019 | Tevs et al. | |
| 11,696,529 B2 | 7/2023 | Yu et al. | |
| 12,063,885 B2 | 8/2024 | Meyers et al. | |
| 2002/0133309 A1* | 9/2002 | Hardt ................ | A01D 41/1277 |
| | | | 702/129 |
| 2005/0225334 A1 | 10/2005 | Rains et al. | |
| 2016/0029561 A1 | 2/2016 | Fischer et al. | |
| 2016/0189007 A1* | 6/2016 | Wellington .......... | G06V 20/695 |
| | | | 382/110 |
| 2017/0013776 A1* | 1/2017 | Palla ...................... | A01F 12/18 |
| 2017/0024876 A1* | 1/2017 | Young ................... | G06Q 50/02 |
| 2017/0094901 A1 | 4/2017 | French, Jr. et al. | |
| 2017/0118914 A1 | 5/2017 | Bruns et al. | |
| 2018/0059034 A1 | 3/2018 | Advani et al. | |
| 2019/0133037 A1 | 5/2019 | Todd et al. | |
| 2019/0137416 A1 | 5/2019 | Todd et al. | |
| 2019/0183047 A1 | 6/2019 | Dybro et al. | |
| 2020/0008351 A1 | 1/2020 | Zielke et al. | |
| 2020/0084966 A1 | 3/2020 | Corban et al. | |
| 2022/0132736 A1 | 5/2022 | Meyers et al. | |

FOREIGN PATENT DOCUMENTS

| | | | |
|---|---|---|---|
| CN | 109328620 A | 2/2019 |
| CN | 110402675 A | 11/2019 |
| DE | 19648126 A1 | 5/1998 |
| EP | 0840109 A2 | 5/1998 |
| EP | 0940656 A1 | 8/1999 |
| EP | 3150048 A1 | 4/2017 |
| EP | 3395154 A1 | 10/2018 |
| WO | WO 2017187249 A1 | 11/2017 |

OTHER PUBLICATIONS

Nelson et al., Microwave Sensing of Moisture Content and Bulk Density in Flowing Grain and Seed, American Society of Agricultural and Biological Engineers, ASABE 59(2): 429-433. (doi: 10.13031/trans.59.11377), 2016. (1 page).

Chung et al., Sensing Technologies for Grain Crop Yield Monitoring Systems: A Review, Journal of Biosystems Eng. 41(4):408-417. (Dec. 2016) https://doi.org/10.5307/JBE.2016.41.4.408, Nov. 25, 2016. (10 pages).

Badaruzzaman Mohamad Noh, Application of Microwave Sensors to Potato Products, A Thesis Submitted to the University of Manchester for the Degree of PhD In Engineering and Physical Science, 2010. (161 pages).

Aayush Bansal et al., PixelNet: Representation of the Pixels, by the Pixels, and for the Pixels, http://www.cs.cmu.edu/~aayushb/pixelNet/, arXiv:1702.06506v1 [cs.CV] Feb. 21, 2017.

Aayush Bansal et al., PixelNet: Towards a General Pixel-Level Architecture, http://www.cs.cmu.edu/~aayushb/pixelNet/, arXiv:1609.06694v1 [cs.CV] Sep. 21, 2016.

Case IH Agriculture, Axial-Flow 250 Series Brochure, AFS Harvest Command, Oct. 2018.

Non-Final Office Action issued in U.S. Appl. No. 17/088,042 dated Dec. 14, 2023.

Berberich, Janine, et al. "Determination of test weight during threshing by analysing air-filled pore volume in grain fills." Landtechnik 74.1 (2019). (Year: 2019).

Chinese Office Action issued in application No. 202111291593.8 dated Jun. 30, 2025.

* cited by examiner

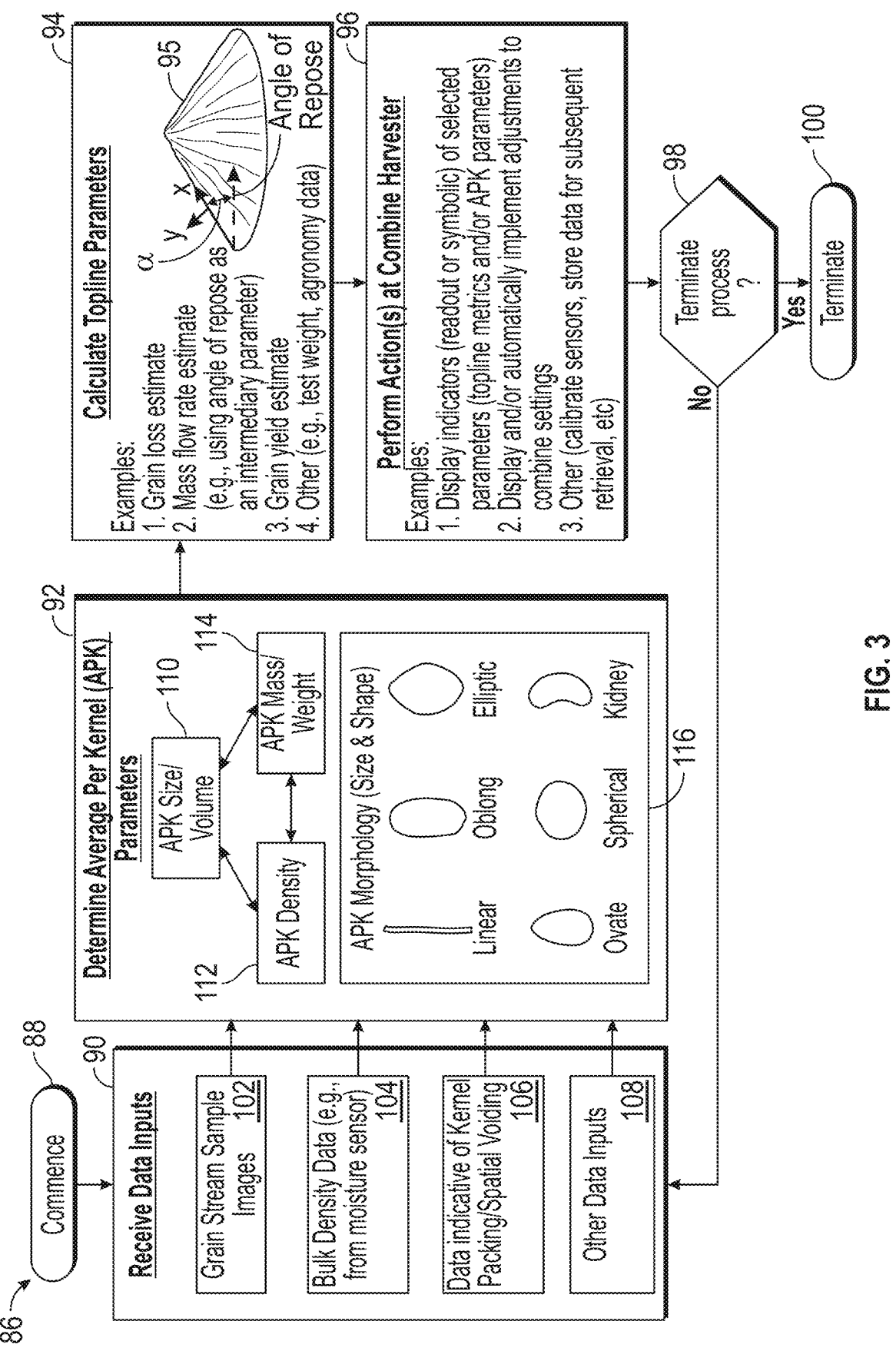

Calculate Topline Parameters — 94

95

Angle of Repose — 96

Examples:
1. Grain loss estimate
2. Mass flow rate estimate (e.g., using angle of repose as an intermediary parameter)
3. Grain yield estimate
4. Other (e.g., test weight, agronomy data)

Perform Action(s) at Combine Harvester

Examples:
1. Display indicators (readout or symbolic) of selected parameters (topline metrics and/or APK parameters)
2. Display and/or automatically implement adjustments to combine settings
3. Other (calibrate sensors, store data for subsequent retrieval, etc)

Determine Average Per Kernel (APK) Parameters — 92

APK Size/Volume — 110

APK Mass/Weight — 114

APK Density — 112

APK Morphology (Size & Shape) — 116

Linear    Oblong    Elliptic

Ovate    Spherical    Kidney

Receive Data Inputs — 90

Grain Stream Sample Images — 102

Bulk Density Data (e.g., from moisture sensor) — 104

Data indicative of Kernel Packing/Spatial Voiding — 106

Other Data Inputs — 108

Commence — 88

86

Terminate process? — 98

No

Yes

Terminate — 100

FIG. 3

KERNEL-LEVEL GRAIN MONITORING SYSTEMS FOR COMBINE HARVESTERS

CROSS-REFERENCE TO RELATED APPLICATION(S)

This is a divisional application of U.S. application Ser. No. 17/088,042, filed Nov. 3, 2020, now allowed.

STATEMENT OF FEDERALLY SPONSORED RESEARCH OR DEVELOPMENT

Not applicable.

FIELD OF THE DISCLOSURE

This disclosure relates to kernel-level grain monitoring systems, which utilize bulk grain sample images and other data to monitor average kernel parameters pertaining to grain harvested and processed by combine harvesters.

BACKGROUND OF THE DISCLOSURE

Combine harvesters (also referred to as "agricultural combines") have greatly improved the efficiency with which corn, canola, soybeans, wheat, oats, sunflowers, and other crops are harvested, threshed, cleaned, and collected for distribution to consumers. Generally, combine harvesters are relatively complex, self-propelled machines capable of harvesting large swathes of crop plants as the harvester travels over a crop field, while separating unbroken grain from broken grain and material other than grain (MOG). After cleaning, the currently-harvested bulk grain is delivered as a "grain stream" into a grain tank, typically by conveyance through a clean grain elevator. Modern combine harvesters often include relatively complex sensor systems capable of providing real-time estimates of grain mass, moisture content, test weight, and other grain quality parameters pertaining to the grain harvested and processed by a given combine harvester. Additionally, grain quality may be monitored utilizing at least one grain camera, which is positioned to capture images of the bulk grain transported through the clean grain elevator (herein, "bulk grain sample images"). Certain combine harvester systems further provide visual tools to assist operators in assessing grain quality when viewing the grain quality image samples on a display screen by, for example, color-coding or otherwise visually distinguish MOG and broken grain from clean, unbroken grain within the grain quality image samples.

SUMMARY OF THE DISCLOSURE

Kernel-level grain monitoring systems for usage onboard combine harvesters are disclosed. In embodiments, the kernel-level grain monitoring system includes a grain camera positioned to capture bulk grain sample images of a currently-harvested grain taken into and processed by a combine harvester, a moisture sensor configured to generate moisture sensor data indicative of a moisture level of the currently-harvested grain, and a display device having a display screen on which parameters pertaining to the currently-harvested grain are selectively presented. A controller architecture is coupled to the grain camera, to the moisture sensor, and to the display device. The controller architecture is configured to: (i) analyze the bulk grain sample images, as received from the grain camera, to determine an average per kernel (APK) volume representing an estimated volume of a single average kernel of the currently-harvested grain; (ii) repeatedly calculate one or more topline harvesting parameters based, at least in part, on the determined APK volume and the moisture sensor data; and (iii) selectively present the topline harvesting parameters on the display device for viewing by an operator of the combine harvester.

In further embodiments, the kernel-level grain monitoring system includes a grain camera positioned to capture bulk grain sample images of a currently-harvested grain taken into and processed by the combine harvester, a moisture sensor configured to generate moisture sensor data indicative of a moisture level of the currently-harvested grain, a display device having a display screen on which parameters pertaining to the currently-harvested grain are selectively presented. A controller architecture coupled to the grain camera, to the moisture sensor, and to the display device. The controller architecture is configured to analyze the bulk grain sample images, as received from the grain camera, to determine an average per kernel (APK) parameter; and determine a target setting adjustment to an actuated harvesting component of the combine harvester based, at least in part, on the APK parameter. Additionally, the controller architecture performs at least one of the following actions: (i) generating a notification, such as visual and/or audible notification, prompting an operator to implement the target setting adjustment, and (ii) controlling the actuated harvesting component to automatically implement the target setting adjustment.

The details of one or more embodiments are set-forth in the accompanying drawings and the description below. Other features and advantages will become apparent from the description, the drawings, and the claims.

BRIEF DESCRIPTION OF THE DRAWINGS

At least one example of the present disclosure will hereinafter be described in conjunction with the following figures:

FIG. 3 is a flowchart of an example process suitably carried-out by a controller architecture of the kernel-level grain monitoring system (FIGS. 1 and 2) to monitor APK parameters pertaining to the bulk grain processed by the combine harvester and to perform other associated actions;

Figure 1:
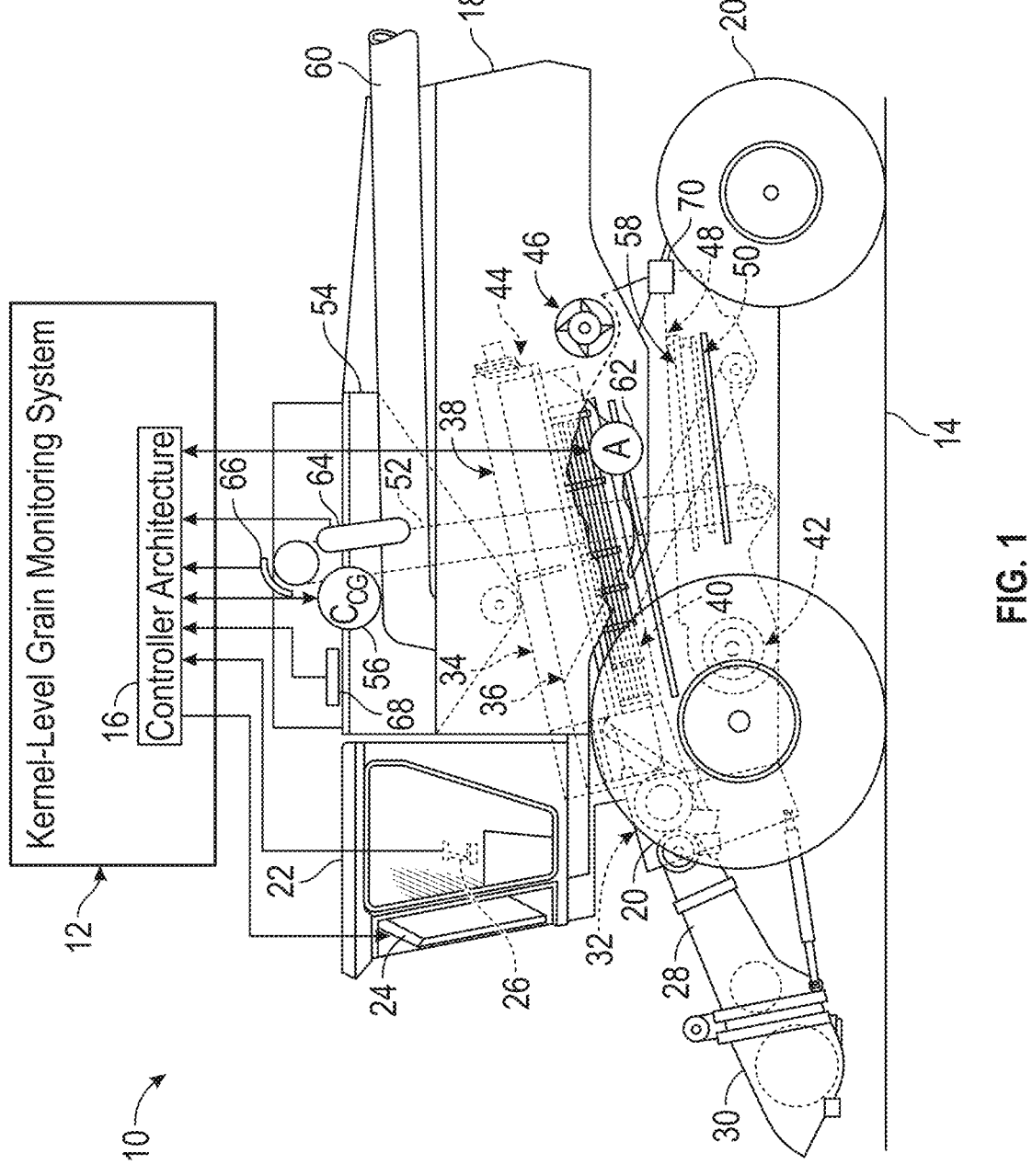
FIG. 1 is a schematic of a combine harvester equipped with a kernel-level grain monitoring system configured to monitor certain average per kernel (APK) parameters for a grain stream processed by the combine harvester, as illustrated in accordance with an example embodiment.

Like reference symbols in the various drawings indicate like elements. For simplicity and clarity of illustration, descriptions and details of well-known features and techniques may be omitted to avoid unnecessarily obscuring the example and non-limiting embodiments of the invention described in the subsequent Detailed Description. It should further be understood that features or elements appearing in the accompanying figures are not necessarily drawn to scale unless otherwise stated.

DETAILED DESCRIPTION

Embodiments of the present disclosure are shown in the accompanying figures of the drawings described briefly above. Various modifications to the example embodiments may be contemplated by one of skill in the art without departing from the scope of the present invention, as set-forth the appended claims.

As appearing throughout this document, the term "kernel" is utilized in a broad or comprehensive sense to encompass all seeds, as well as edible portions of other food crops, which are harvested and processed utilizing combine har-vesters. So defined, the term "kernel" encompasses the seeds of grass food crops, such as barely, corn, oats, and wheat; soybeans and other bean plant seeds; and the seeds of other plant types including buckwheat, millet, quinoa, rapeseed, rice, and sunflower seeds. In comparison, the terms "grain" and "bulk grain" are utilized interchangeably to refer to kernels in bulk, particularly as processed and temporarily stored by a combine harvester or other harvesting machine. Finally, the term "grain stream" refers to a body of bulk grain, typically containing varying amounts of other crop material, in motion as the bulk grain is transported from one location to another within a combine harvester.

Overview

As noted above, combine harvesters are commonly equipped with relatively complex sensor systems, which enable real-time grain quality monitoring as a given com-bine harvester engages in active harvesting; that is, as the combine harvester travels across swaths of a field, ingests harvested crop plants, processes (threshes and cleans) the crop plants to generate a bulk grain stream, and ultimately directs the bulk grain stream into a grain tank for temporarily storage. To aid in grain quality grain assessment, the com-bine harvester may include at least one grain camera, which is positioned adjacent the clean grain elevator and which captures live images of the grain stream carried by the clean grain elevator to the grain storage tank. Further, certain visual tools have been developed enabling combine har-vester operators to not only view the live camera images captured by such grain cameras, but that further augment the live camera images with color-coding (or similar visual enhancements) to aid operators in visually distinguishing clean, unbroken grain from undesirable material (e.g., for-eign material and broken grain) entrained within the bulk grain stream. A similar approach may also be employed in conjunction with a tailings camera, which is positioned to capture images of the tailings discharged from the rear of the combine harvester and which is usefully viewed by an operator when assessing grain losses.

Through the provision of such visual tools, combine harvester operators may gain an increased awareness of grain quality at a given juncture in time as a combine harvester travels over different regions of a field and oper-ates in accordance with current setting values. This, in turn, may enable an operator to better pilot a given combine harvester by, for example, adjusting combine settings to minimize grain loss, improve grain quality, or otherwise enhance overall performance aspects of combine harvester operation. Aside from the provision of such visual tools, combine harvester systems further monitor certain funda-mental or key harvesting parameters pertaining to combine harvester efficiency and harvesting productivity levels. Such parameters are referred to herein as "topline harvesting metrics" and include grain yield, grain loss, test weight, grain mass flow rate estimates, grain constituent informa-tion, and other parameters. Generally, such topline harvest-ing metrics are calculated utilizing data inputs provided by multiple sensors integrated into a given combine harvester and data received from other sources, such as operator-entered data or, perhaps, data received from a backend service over a wireless datalink, such as a telematics gate-way module. Pertinent sensor data for calculating topline harvesting metrics may include data gathered from one or more moisture sensors onboard a combine harvester, grain loss sensors (e.g., strike plate sensors positioned at the aft end of the shoe and/or outlet end of a clean grain elevator of a combine harvester), mass flow rate sensors, grain tank load cells, and grain elevator speed sensors, to list but a few examples. Such topline harvesting metrics may be repeat-edly calculated or assessed on a real-time or near real-time basis, and the instantaneous values of the topline harvesting metrics may be displayed for consideration by the combine harvester operator. Additionally, such topline harvesting metrics can be compiled with other data (e.g., temporal and global positioning system (GPS) data) and stored as histori-cal datasets to, for example, produce yield maps and similar data-driven resources aiding in optimizing seeding and growing operations. Finally, in certain cases, combine har-vester systems may utilize such data inputs to determine and automatically implement target adjustments for actuated harvesting components, such as shoe, sieve, fan, and chaffer components, onboard a given combine harvester.

In the above-described manner, grain monitoring systems integrated into modern combine harvesters supply combine harvester operators with fundamental, real-time information assisting in operator decision-making when piloting a com-bine harvester within dynamic environments. Additionally, certain existing combine automation systems further enhance combine harvester performance through automated, on-the-fly fine tuning of combine harvester settings. This notwithstanding, relatively high degrees of inaccuracies can develop in the topline harvesting metrics and other datasets calculated by current combine harvester display and auto-mation systems. This may be due, in part, to the usage of certain standardized (assumed) values for certain key input parameters or crop attributes utilized in calculating topline harvesting metrics. As an example, existing combine har-vester display and automation systems may utilize pre-defined kernel weight and size assumptions in calculating key crop attributes, such as a predefined (assumed) 1000 kernel test weight; that is, the weight of 1000 kernels when packed into a volumetric bushel equal to 1.244 cubic feet or 0.035 cubic meters. Kernel weight and size can, however, vary significantly in conjunction with changing crop condi-tions. Consequently, reliance upon such assumed or gener-alized data inputs can introduce undesired inaccuracies in calculating topline harvesting metrics and other data param-eters. In the aggregate, such inaccuracies can detract from the overall quality of information presented to combine harvester operators, while reducing combine harvester per-formance when on-the-fly adjustments to combine harvester settings are automatically implemented based upon this information.

An ongoing industry demand thus exists for combine harvester systems capable of improving the accuracy and consistency with which relevant data parameters are calculated during combine harvester operation, particularly topline harvesting metrics. Ideally, such a combine harvester system would improvement the quality and consistency of data calculations, while utilizing existing sensor arrays onboard combine harvesters to minimize implementations costs and streamline customer adoption. Embodiments of such combine harvester systems are provided herein and referred to as "kernel-level grain monitoring systems." As indicated by the descriptor "kernel-level," the kernel-level grain monitoring systems enable the monitoring of certain unique data parameters considered on an average, single kernel basis; that is, such that a given data parameter describes a single kernel, on average (mean or medium), within the grain stream composed of the bulk grain currently harvested utilizing the combine harvester. Such per kernel parameters are referred to as average per kernel parameters or "APK parameters," denoting that the APK parameters represent average values or estimates of the kernels contained in a given bulk grain stream generated as a combine harvester processes crop plants during active harvesting. In embodiments, the APK parameters can be extrapolated or otherwise utilized to better inform topline harvesting metrics, such as grain loss, grain yield, test weight, grain constituent, and mass flow rate estimates, calculated during combine harvester operation. This, in turn, may improve the quality of information displayed to combine harvester operators (or stored for subsequent analysis); and, when applicable, the precision with which target adjustment settings to actuated components of the combine harvester are determined and potentially automatically implemented by the combine harvester system.

Generally, embodiments of the kernel-level grain monitoring system utilize imagery captured from at least one grain camera, along with other pertinent data inputs, to track one or more of the following APK parameters: (i) APK volume, (ii) APK density, (iii) APK weight or mass, and (iv) APK morphology. As appearing herein, the terms "APK volume," "APK density," and "APK weight (or mass)" represent an estimated per kernel average of the volume, density, and weight (or mass) of the kernels contained in the grain stream generated during combine harvester operation. Comparatively, the term "APK morphology" refers to an average kernel shape (including angularity) and size of the kernels within the bulk grain stream subject to analysis. For example, in embodiments, the APK morphology may be expressed in terms of a classification or categorization based upon a generalized, three dimensional shape (and possible size) of the kernels contained in the grain stream, such as a large spherical classification or a small oblong classification. Additional description in this regard is provided below in connection with FIG. 3.

Regarding APK volume, the kernel-level grain monitoring systems may monitor this APK parameter via dimensional image analysis of the bulk grain sample images captured by the grain camera; and, specifically, by estimating and averaging certain dimensional parameters (e.g., average length and diameter) of the kernels visually detected within the bulk grain sample images. Additional data may also be considered in calculating an estimated APK volume in embodiments, such as image depth data (if available) and any available morphology information pertaining to the currently-harvested grain. In this latter regard, a combine harvester operator may input data into the kernel-level grain monitoring system specifying a grain type of the currently-harvested grain, which may, in turn, be utilized to establish a kernel shape category or classification; e.g., linear, oblong, elliptic, ovate, spherical, or other three dimensional kernel shape category. This information may then be considered by the kernel-level grain monitoring system in assessing the APK volume of the kernels depicted in the bulk grain sample images. Additionally or alternatively, the kernel-level grain monitoring systems may establish an APK morphology of the bulk grain by visual analysis of the bulk grain sample images themselves, whether performed onboard the combine harvester or offboard the combine harvester by a remote data source (e.g., a backend service) in wireless communication with the kernel-level grain monitoring system over a network.

Embodiments of the kernel-level grain monitoring system further usefully, although non-essentially, monitor APK density and/or APK weight (or mass) of the kernels within the bulk grain stream utilizing APK volume as an input. In the case of APK density, the kernel-level grain monitoring systems can determine this parameter as a function of APK volume and a suitable bulk density parameter pertaining to the bulk grain stream. In embodiments, the bulk density parameter can be entered by an operator or recalled from memory as a standardized value associated with a particular crop type, based upon historical (e.g., georeferenced) data, or based upon other input data. More usefully, however, a bulk density measurement may be obtained utilized data provided by onboard sensors of the type commonly integrated into modern combine harvesters, such as a grain moisture sensor. In this latter regard, existing moisture sensors monitor data from which bulk densities of sampled grain volumes can be obtained or determined from capacitance-based moisture level readings. For example, in the case of a capacitance-type moisture sensor, a fraction of the bulk grain stream may be directed into or through a known volume of space bordered by electrodes. The capacitance across this sampled volume of the grain stream is measured and converted to a bulk weight density for the grain stream, which is commonly expressed in terms of weight per volume (pounds per bushel). Traditionally, such a bulk weight density measurement is utilized for purposes other than those described herein; e.g., to convert mass or weight yield estimates (commonly expressed in mass or weight per area) to volumetric yield estimates (commonly expressed in volumetric bushels per acre) in generating grain yield maps. Embodiments of the kernel-level grain monitoring system may leverage the availability of this sensor data (or other sensor data indicative a bulk density measurement of the currently-harvested grain), in addition to the above-described APK volume parameter, to calculate and track the APK density of the currently-harvested grain on a real-time basis. In a similar regard, the APK weight (or mass) can be readily calculated as a function of APK volume and a bulk weight (or mass) parameter obtained from sensor data onboard the combine harvester, such as strike plates positioned at the outlet end of the clean grain elevator, load cells located within the grain tank, or other sensors from which bulk weight (or mass) measurements pertaining to the currently-harvested grain can be derived.

Embodiments of the kernel-level grain monitoring systems may utilize any or all of the above-described APK parameters to better inform (improve the accuracy of) topline harvesting metrics. Grain loss estimates can be improved by considering the APK mass or weight parameters when, for example, grain loss is calculated utilizing strike plate sensors placed at certain locations in the combine harvester, typically at the shoes and separator sections of a combine harvester. Specifically, in at least some embodiments, the APK weight can be scaled upwardly to a 1000 kernel weight value, which can be utilized in place of the standardized 1000 kernel weight value utilized by existing automation systems and known to cause errors approaching or exceeding 35% in grain loss estimate calculations. Through the usage of 1000 kernel weight values (or other APK parameter-based weight or mass parameters) more in keeping with "ground truth" conditions, grain loss parameters can be calculated at higher accuracies and with greater consistency. This, in turn, may enable improvements in grain loss mapping and grain loss performance target calibration processes by reducing field-to-field variances.

So too may the above-mentioned APK morphology, particularly kernel size, be considered to enhance the accuracy with which grain size is classified as opposed to the conventional practice of utilizing standard (assumed) value or operator input selecting among a limited number of size classifications. Similarly, mass flow rate measurements can be enhanced utilizing the APK weight and/or APK density values calculated by the kernel-level grain monitoring system depending upon relevant factors; e.g., whether mass flow rate is measured by measuring impacts against a strike plated positioned at the outlet end of the clean gain elevator (in addition to other factors, such as elevator belt speed), utilizing a grain camera to estimate the rate which grain is transported through the clean grain elevator, or in another manner. In certain cases, the angle of repose (indicative of grain pile height) may also be better informed utilizing APK morphology to, for example, enhance calibration of the mass flow rate sensor utilizing data provided by the grain tank load cells, as discussed below in connection with FIG. 3. Dry yield estimates, which are often calculated utilizing mass flow rate and other factors (e.g., header width, combine ground speed or velocity, and moisture data), may likewise be improved through improvements in the mass flow rate estimates. Additionally, the APK morphology (particularly size) and APK weight may allow seed producers and growers to improve their product and services from an agronomical perspective. Finally, a kernel packing indicator or conversion factor may be determined and considered to compensate for the air void volume in a given volume of space packed with the bulk grain currently harvested by the combine harvester when the APK parameters are extrapolated or upscaled to arrive at certain, commonly-utilized bulk grain parameters, such as test weight.

Any combination of the APK parameters and topline harvesting metrics mentioned above can be presented on a display screen within the cabin of the combine harvester for operator viewing; e.g., depending upon operator navigation between different graphical user interface (GUI) screen or pages displaying such information. Such information can also be stored and recalled at a later date for post-harvesting analysis to, for example, enable operators and growers to view yield maps, grain loss maps, and similar agronomy analysis tools useful in refining procedures and practices relating to field preparation, seeding, maintenance (treatment), and harvesting stages of growing operations. Additionally, such information may be utilized to determine target adjustments to combine harvester settings and either: (i) prompt operators to implement the determined target adjustments (e.g., via visual cues generated on a display device within the cabin of the combine harvester, via audible cues, or a combination thereof), or (ii) automatically implement target adjustments to actuated harvesting components or devices onboard the combine harvester in an automated, on-the-fly manner. In this latter regard, the kernel-level grain monitoring systems may determine and automatically implement adjustments to shoe positioning, sieve positioning, chaffer positioning, and fan speeds, and/or similar combine harvester settings in at least some implementations. As a specific, albeit non-limiting example, relatively fine adjustments can be implemented to fan speeds to, for example, increase fan speeds in conjunction with increasing APK weight considering the reduced tendency of heavier kernels to be carried away by the airstream and discharged from the combine harvester. Further, in certain cases, corresponding adjustments may also be made to shoe, sieve, and/or chaffer positioning to facilitate airflow in conjunction with increasing fan speeds.

Examples of the kernel-level grain monitoring system will now be described in the context of an example combine harvester, as illustrated and discussed below in connection with FIGS. 1 and 2. Additionally, example methods or processes suitably carried-out by the controller architecture of the kernel-level grain monitoring system to monitor multiple APK parameters, display one or more topline harvesting metrics calculated utilizing the APK parameters, and perform other actions is described below in connection with FIGS. 3 and 4. Finally, examples of manners in which APK parameters, topline harvesting metrics calculated utilizing APK parameters, and suggested combine setting adjustments determined utilizing the APK parameters can be displayed to operators of a combine harvester are discussed below in connection with FIG. 5. The following description is provided by way of non-limiting illustration only and should not be construed to unduly restrict the scope of the appended Claims in any manner.

Combine Harvester Equipped with Example Kernel-Level Grain Monitoring System

Referring to FIG. 1, a combine harvester 10 equipped with a kernel-level grain monitoring system 12 is schematically depicted in accordance with an example embodiment of the present disclosure. The combine harvester 10 is presented by way of illustration to establish a non-limiting example context in which embodiments of the kernel-level grain monitoring system 12 may be better understood. In further embodiments, the combine harvester 10 may assume other forms and may include different combinations of components suitable for processing crop plants ingested into the harvester 10 when traveling over a field 14, while engaged in active harvesting. Further, only selected components of the kernel-level grain monitoring system 12, such as a controller architecture 16, are shown in FIG. 1 for illustrative clarity. Further illustration and discussion of the example kernel-level grain monitoring system 12 is provided below in connection with FIGS. 2-5.

The example combine harvester 10 includes a chassis body or mainframe 18, which is supported by a number of ground-engaging wheels 20. The ground-engaging wheels 20 are powered by a non-illustrated engine and drivetrain including, for example, an electronically-controlled hydraulic transmission. Atop a forward portion of the main frame 18, a cabin 22 encloses an operator station including an operator's seat (not shown), at least one display device 24, and an operator interface 26. A feederhouse 28 is mounted to a forward portion of the main frame 18 of the combine harvester 10 at an elevation generally below the cabin 22. Various harvesting heads or, more simply, "headers" are attachable to the feederhouse 28 in an interchangeable manner to, for example, allow customization of the combine harvester 10 for harvesting a particular crop types. An example of one such header, here a harvesting platform 30, is shown in FIG. 1.

As the combine harvester 10 travels over the field 14 in a forward direction, the harvesting platform 30 gathers severed crop plants into the feederhouse 28, which then consolidates the severed crop plants for conveyance (e.g., via a non-illustrated conveyor belt contained in the feederhouse 28) into the interior of the combine harvester 10. Within the combine harvester 10, the crop plants are engaged by a rotating drum conveyor or "beater" 32, which directs the crop plants in a generally upward direction into a rotary threshing and separating section 34. The rotary threshing and separating section 34 can include various components for performing the desired functions of separating the grain and chaff from other plant material. The illustrated rotary threshing and separating section 34, for example, includes a rotor or drum 36 having threshing features and rotatably mounted in a case or rotor housing 38. Rotation of the threshing drum 36 within the rotor housing 38 causes both grain and chaff to fall through the separation grates of a concave 40 and into the inlet of a lower grain cleaning section 42. Concurrently, straw and similar MOG is directed toward an outlet end 44 of the rotary threshing and separating section 34 and is ultimately delivered to another rotating drum or "discharge beater" 46 for expulsion from an aft end of the combine harvester 10.

Discussing now the grain cleaning section 42 in greater detail, this section of the combine harvester 10 includes various components adapted to clean the newly-harvested grain, while separating the chaff therefrom. Such components may include a chaffer 48, a sieve 50, and any number of fans, such as a centrifugal blower fan or wheel 78 shown in FIG. 2. By action of the grain cleaning section 42, the newly-cleaned grain is directed into a clean grain elevator 52 for conveyance upwardly into a storage reservoir or grain tank 54 of the combine harvester 10. The path traveled by the clean grain from the grain cleaning section 42 to the grain tank 54 is referred to herein as a "clean grain flow path," while the grain traveling along this flow path is generally referred to as a "clean grain stream." The grain and MOG traveling through the combine harvester 10, generally, is more broadly referred to herein as a "grain stream." Thus, the "clean grain stream" is a segment of the larger grain stream after threshing, separation, and cleaning. At least one camera 56 is positioned to capture imagery (herein, "bulk grain sample images") of the grain transported along the grain stream and, specifically, the clean grain stream in embodiments. In this regard, and indicated in FIG. 1, the grain camera 56 may be positioned adjacent the clean grain elevator 52 to capture imagery of the bulk grain stream transported via the elevator 52 into the grain tank 54. In other embodiments, one or more additional cameras may be positioned at differing locations along the clean grain stream (e.g., at two or more locations to capture imagery of the clean bulk grain transported via the elevator 52), with the imagery data processed and averaged or otherwise blended to yield the below-described APK parameters. It is also possible for the grain camera 56, or an associated sensor system, to provide depth data useful in dimensionally assessing the kernels within the bulk grain sample images in embodiments. When applicable, such depth data may assume the form of direct, transducer-based depth measurements (e.g., as captured by an acoustic sensors, radar-based sensors, or similar sensors detecting reflected energy or sonar pulses), as well as other image data from which depth may be inferred (e.g., as captured by a stereoscopic camera assembly).

As the clean grain elevator 52 transports the newly-harvested grain into the grain tank 54, tailings fall onto a return elevator 58 extending across a lower portion of the clean grain elevator 52. The return elevator 58 then recycles the tailings back to the inlet of the threshing drum 36 for further threshing to allow the above-described grain processing steps to repeat and maximize the grain yield of the combine harvester 10. In this manner, the combine harvester 10 effectively intakes severed crop plants from the field 14, extracts grain from the crop plants, cleans the newly-extracted grain, and then stores the grain in grain tank 54 for subsequent unloading utilizing, for example, an unloading auger 60. Also, during usage of the combine harvester 10, certain components within the combine harvester 10 may be positionally adjusted or the operating parameters of such components may be modified utilizing any number of actuators 62, such as hydraulic- or electrically-controlled linear or rotary actuators, one of which is generically represented by symbol 62 in FIG. 1. In this regard, the operational speeds of any number of fans or conveyor belts may be varied, as may the position of any number of non-illustrated deflectors, chaffer components, sieve components, shoe components, or the like. Such actuators 62 may be controlled in response to operator input received via the operator interface 26 located within the cabin 22, controlled via command signals issued by the controller architecture 16 included in the kernel-level grain monitoring system 12, or otherwise commanded by another controller or control unit onboard the combine harvester 10.

The combine harvester 10 contains various other sensors in addition to those mentioned above, which may supply data to the controller architecture 16 during operation of the kernel-level grain monitoring system 12. A non-exhaustive list of such additional onboard sensors includes at least one grain moisture sensor 64 for providing data indicative of the moisture levels within the currently-harvester grain and, in certain cases, capacitance measurements indicative of a bulk density of the grain; e.g., expressed in pounds (lbs.) per bushel. One or more mass flow sensors, which may assume the form of one or more strike plates 66 mounted adjacent the outlet end of the clean grain elevator 52 and positioned to be impacted by the kernels ejected from the elevator 52 into the grain tank 54. In other embodiments, the mass flow sensor(s) onboard the combine harvester 10 may be implemented utilizing another technology or approach including, for example, by image analysis of the camera feed provided by the grain camera 56. Additionally, the combine harvester 10 may include a number (e.g., three or more) load cells 68 located in the grain tank 54 and utilized weigh stored grain to, for example, calibrate the mass flow sensor 66. The combine harvester 10 may also include various sensors for measuring grain loss, such as one or more shoe loss sensors 70 (e.g., strike plate sensors) and/or non-illustrated (e.g., strike plate) sensors positioned at the separators, in at least some embodiments. Various other non-illustrated sensors can also be deployed onboard the combine harvester 10, as conventional, such as sensors for monitoring the speed of and/or the load placed on the clean grain elevator 52. Additionally cameras, such as a tailing elevator camera 72, may also be integrated into the combine harvester 10 in embodiments, with the video feed supplied by such cameras selectively presented on a display screen of the display device 24, as described more fully below in connection with FIG. 2.

Figure 2:
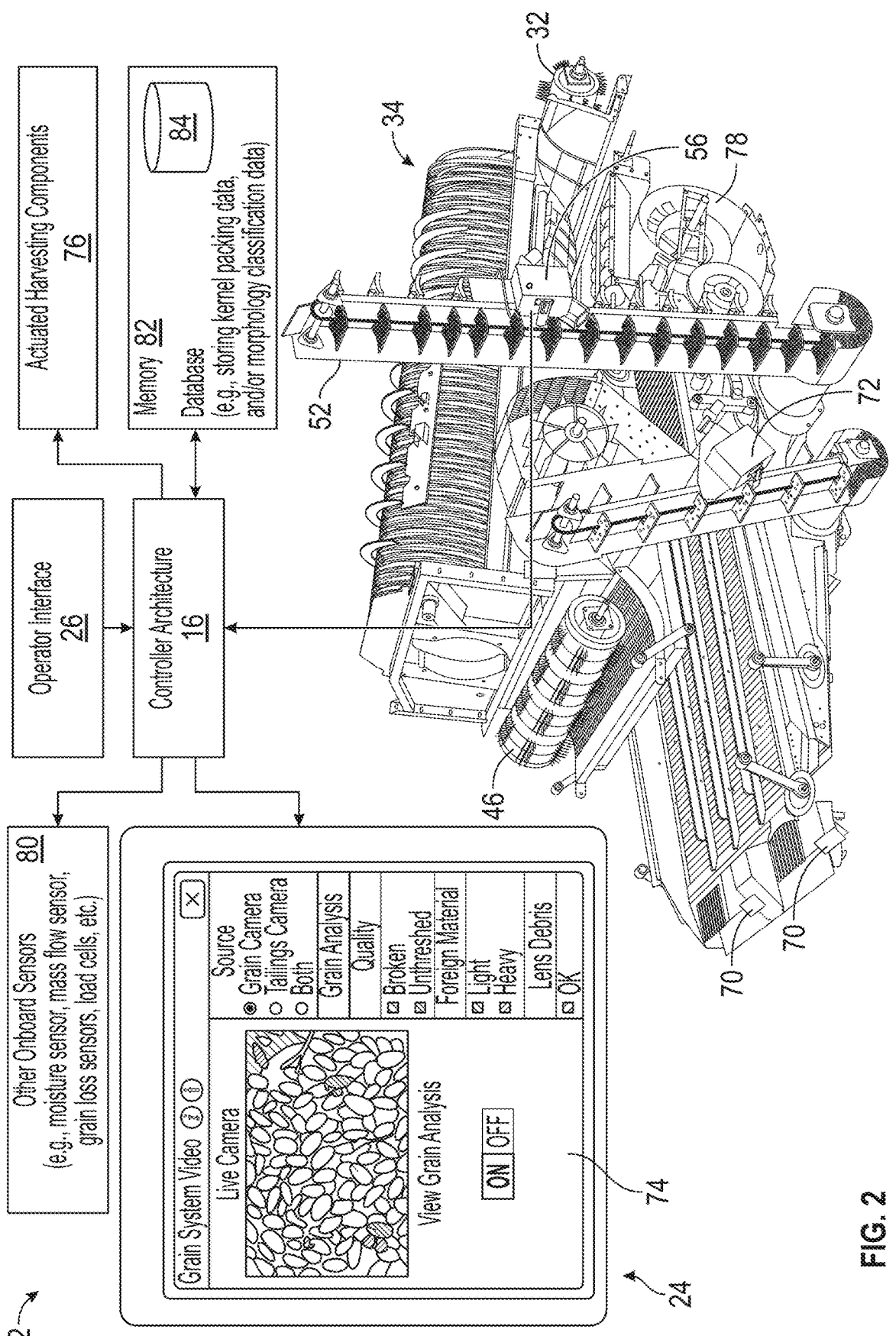
FIG. 2 schematically illustrates additional components suitably included in embodiments of the example kernel-level grain monitoring system.

Referring now to FIG. 2, the kernel-level grain monitoring system 12 is shown in greater detail, as is certain internal harvesting machinery of the combine harvester 10. Reference numerals are carried-over from FIG. 1, where appropriate, noting that schematic representations of the controller architecture 16, the display device 24, and the operator interface 26 are presented in this drawing figure. Additionally, the kernel-level grain monitoring system 12 is depicted as including "actuated harvesting components 76," which generically encompasses those components involved in ingesting and processing crop plants to yield a grain bulk stream during combine harvester operation, as previously described. Accordingly, in the illustrated schematic, the actuated harvesting components 76 can include any combination of actuated sieve, shoe, deflectors, or chafer components adjusted utilizing the actuators 62 generically shown in FIG. 1, as well as a centrifugal fan or blower wheel 78 shown in the bottom right of FIG. 2. Similarly, the generically-depicted onboard sensors 80 encompass those sensors integrated into the combine harvester 10 aside from the grain camera 56, including the above-described grain moisture sensor 64, the mass flow sensor (e.g., the strike plate sensors 66), the grain tank load cells 68, and the shoe loss sensors 70. In addition to the foregoing components, the kernel-level grain monitoring system 12 further includes a computer-readable memory 82 storing a database 84, which may contain packing density factors, morphology classification data, and other stored data utilized by the controller architecture 16 in carrying-out the processes described below. The various data connections between these components are represented in FIG. 2 by a number of signal lines terminating in arrowheads, with such signal lines generally representative of any combination of wired or wireless data connections.

The controller architecture 16 of the kernel-level grain monitoring system 12 can assume any form suitable for performing the functions described throughout this document. The term "controller architecture," as appearing herein, is utilized in a non-limiting sense to generally refer to the processing architecture of kernel-level grain monitoring system 12. The controller architecture 16 can encompass or may be associated with any practical number of processors, control computers, computer-readable memories, power supplies, storage devices, interface cards, and other standardized components. The controller architecture 16 may also include or cooperate with any number of firmware and software programs or computer-readable instructions designed to carry-out the various process tasks, calculations, and control/display functions described herein. Such computer-readable instructions may be stored within a non-volatile sector of the memory 82 along with the below-described database or databases 84. While generically illustrated in FIG. 2 as a single block, the memory 82 can encompass any number and type of storage media suitable for storing computer-readable code or instructions, as well as other data utilized to support the operation of the kernel-level grain monitoring system 12. The memory 82 may be integrated into the controller architecture 16 in embodiments as, for example, a system-in-package, a system-on-a-chip, or another type of microelectronic package or module.

The operator interface 26 located within the cabin 22 of the combine harvester 10 can be any device or group of devices utilized by an operator to input commands into or otherwise control the kernel-level grain monitoring system 12. In various implementations, the operator interface 26 may be integrated into or otherwise associated with the display device 24. In this regard, the operator interface 26 may include physical inputs (e.g. buttons, switches, dials, or the like) located on or proximate the display device 24, a touchscreen module integrated into the display device 24, or a cursor input device (e.g., a joystick, trackball, or mouse) for positioning a cursor utilized to interface with GUI elements generated on the display device 24. Comparatively, the display device 24 can be any image-generating device configured for operation within the cabin 22 of the combine harvester 10. The display device 24 may be affixed to the static structure of the combine harvester cabin 22 and realized in a head-down display (HDD) configuration in embodiments. An example of a GUI screen 74 presenting a live image of the grain stream, as captured by the grain camera 56, is shown in FIG. 2. As can be seen, various operator-selectable options may also be produced on the GUI screen 74 to, for example, enable an operator to switch between presentation of the camera feeds obtained from the grain camera 56 and the tailings camera 72, to apply a visually-augmented grain quality analysis tool (applying color-coding to broken grain and MOG detected in the live camera image), and to perform other functions, such as providing visual advisory alerts regarding excessive lens debris.

During operation of the kernel-level grain monitoring system 12, the controller architecture 16 performs certain processes to monitor (repeatedly calculated) one or more APK parameters and further perform certain actions in conjunction with monitoring of the APK parameters. Such actions may include generating various graphics, numerical read-outs, symbological elements, or GUI screen presented on the display screen of the display device 24 depending upon, for example, operator navigation to a particular GUI screen. A selected GUI screen generated on the display device 24 may present calculated APK parameter(s), topline harvesting metrics (e.g., a grain loss estimate, a grain mass flow rate estimate, or a grain yield estimate) calculated utilizing the calculated APK parameter(s), and/or other such information directly or indirectly pertaining to the APK parameters. Corresponding audible alerts or advisory notifications can also be generated in conjunction, or in lieu of, such visual notifications presented on the display screen 24. Additionally or alternatively, embodiments of the kernel-level grain monitoring system 12 may determine target setting adjustments to actuated harvesting components of the combine harvester 10 utilizing (that is, based at least in part on) the instantaneous values or trends of APK parameters; the instantaneous values or trends of topline harvesting metrics; or any blended combination thereof. When such target setting adjustments are determined, the controller architecture 16 may prompt an operator of the combine harvester 10 to implement the target setting adjustments via generation of suitable graphics on the display device 24, via generation audible notifications (e.g., audible annunciation, chimes, or other audible cues), and/or via generation of any other operator-perceived cues (e.g., haptic notifications). In other instances, the controller architecture 16 may automatically implement target setting adjustments in an on-the-fly or automated manner, while generating graphics on a given GUI display screen (and/or generating accompanying audible notifications or advisory alerts) notifying the combine harvester operator when such automated adjustments are performed. Other actions can also be performed by the controller architecture 16 in conjunction with determining and applying the APK parameters, as further described below in connection with an example kernel-level grain monitoring process set-forth in FIG. 3.

Referring now to FIG. 3, a kernel-level grain monitoring process 86 is presented in accordance with a non-limiting example embodiment of the present disclosure. The kernel-level grain monitoring process 86 can be carried-out by the controller architecture 16 of the kernel-level grain monitoring system 12 in embodiments of the present disclosure and is principally described below as such; however, in alternative implementations, it is possible for at least some process steps of the kernel-level grain monitoring process 86 to be carried-out by a remote network-connected source (e.g., a backend service, such a cloud-based support service) in communication with the kernel-level grain monitoring system 12 via a suitable wireless transceiver or datalink (e.g., a telematics gateway module) onboard the combine harvester 10. The kernel-level grain monitoring process 86 includes a number of process STEPS 88, 90, 92, 94, 96, 98, 100, each of which is described, in turn, below. Depending upon the particular manner in which the kernel-level grain monitoring process 86 is implemented, each step generically illustrated in FIG. 3 may entail a single process or multiple sub-processes. Further, the steps illustrated in FIG. 3 and described below are provided by way of non-limiting example only. In alternative embodiments of the kernel-level grain monitoring process 86, additional process steps may be performed, certain steps may be omitted, and/or the illustrated process steps may be performed in alternative sequences.

The kernel-level grain monitoring process 86 commences at STEP 88 in response to the occurrence of a predetermined trigger event. In certain instances, the trigger event may be detection of the intake of severed crop plants into the combine harvester 10. In other instances, the kernel-level grain monitoring process 86 may commence in response to a different trigger event, such as in response to operator input received via operator interface 26 indicating that the kernel-level grain monitoring process 86 is desirably performed. After commencing (STEP 88), the controller architecture 16 of the kernel-level grain monitoring process 86 advances to STEP 90 during which the controller architecture 16 gathers current data inputs utilized in performing subsequent steps of the process 86. Such data inputs can be recalled from the memory 82 (including recollection of information stored in the database 84); entered by an operator utilizing the operator interface 26; received from any number of the sensors onboard the combine harvester 10; and, perhaps, received from a cloud-based backend service or other remote data source over a non-illustrated datalink, such as a modular telematics gateway onboard the combine harvester 10. Examples of such data inputs are identified on the left side of FIG. 3 and include one or more bulk grain sample images 102 captured by the grain camera 56 during or immediately prior to the current iteration of the kernel-level grain monitoring process 86, bulk grain density data 104 pertaining to the currently-harvested grain, data indicative of kernel packing 106 (also referred to herein as a "kernel packing factor"), and any number of additional data inputs 108, such as manually-entered data received from an operator of the combine harvester 10.

As noted above, the bulk grain sample images 102 can be assume the form of any image data captured of the currently-harvested grain by the grain camera 56 during operation of the combine harvester 10. In the illustrated example, this includes the bulk grain sample images 102 captured by the grain camera 56 as the bulk grain stream is transported upwardly through the clean grain elevator 52 and into the grain tank 54 of the combine harvester 10. In other instances, bulk grain sample images may be captured by multiple cameras deployed onboard the combine harvester 10 at any number of locations. It is also possible to supplement the below-described image analysis performed utilizing the imagery captured by the grain camera 56 with image analysis of the imagery captured by the tailings camera 72 in at least some embodiments; however, in other embodiments, only the imagery from the grain camera 56 may be considered as this imagery depicts the grain stream in a clean state, which is largely free of broken grain and MOG, to ease image analysis in distinguishing unbroken grain kernels from other materials (e.g., broken kernels and MOG) within the captured imagery. Finally, as previously indicated, the grain camera 56 can potentially captured image data outside of the visible portion of the electromagnetic spectrum and/or may gather depth data (e.g., when two cameras are situated in a stereoscopic relationship) in at least embodiments of the present disclosure.

As generically illustrated in FIG. 3, the bulk density data 104 can assume the form of any data indicative of the volumetric density of the currently-harvested when packed into a given volume of space. In embodiments, the bulk density data 104 can be a default value recalled from memory based upon a type of grain currently-harvested by the combine harvester 10, as may be determined by operator input or perhaps ascertained by the controller architecture 16 via image analysis of the grain camera imagery or utilizing other onboard sensor inputs. In this case, the controller architecture 16 may recall a particular value from the database 84 stored in the computer-readable memory 82 based upon a currently-harvested grain type; and then utilize this value in calculating the APK density value in the manner described below. In other instances, the bulk density data 104 can be directly entered into the kernel-level grain monitoring system 12 by an operator via operator interface 26. Such possibilities notwithstanding, the bulk density data 104 is usefully obtained directly from one or more sensors onboard the combine harvester 10 when possible. To this end, in embodiments in which a combine harvester is equipped with a suitable moisture sensor, data from the moisture sensor (e.g., the moisture sensor 64 generically shown in FIG. 1) can be utilized to determine a bulk density of the currently-harvested grain stream. In addition to providing data indicative of the moisture content of the currently-harvested grain, generally, the moisture sensor 64 may be capable of measuring a sample capacitance of the bulk grain stream, which can then be converted to a bulk density measurement for performing the processes or calculations described below.

Data indicative of kernel packing 106 can also be gathered during STEP 90 of the kernel-level grain monitoring process 86. When collected, such kernel packing data 106 may assume the form of any information useful in assessing the fraction of space occupied by solid mass (the kernels of the currently-harvested grain stream) when packed into a given volume of space, as compared to the cumulative void space of the spatial volume. When utilized, the kernel packing indicator can be determined through empiric testing, which case a range of packing indicator values may be stored corresponding to a range of APK morphologies. Specifically, in embodiments, the kernel packing data 106 may be determined based upon a morphological classification (e.g., size and shape) of the currently-harvested grain, whether determined by a recollection from a two-dimensional lookup table or other data structure stored in the memory 82 based upon the currently-harvested grain type, based upon operator data input, or determined in another manner. In other instances, the controller architecture 16 may perform further image analysis of the bulk grain sample images to measure or estimate the cumulative air voiding in the imagery (e.g., the air voiding discerned in the visible regions of grain piles carried by the paddles of the clean grain elevator 52) and extrapolate voiding to a percentage or fraction of a three dimensional volume of space occupied by air voids, as opposed to solid matter (kernels), when packed with kernels from the sampled grain stream. In still other embodiments, the kernel packing indicator may be determined in another manner.

Finally, various other data inputs 108 can be collected during STEP 90 of the kernel-level grain monitoring process 86. Such data inputs 108 can include other types of operator input data, historical data, and other sensor data useful in calculating the APK parameters and the topline harvesting metrics described below in connection with STEP 94. For example, data indicative of the mass flow rate may be collected from any suitable type of mass flow rate sensor (e.g., the strike plate sensor 66 shown in FIG. 1), data indicative of grain loss may be collected from the shoe loss sensors 70 (or another type of grain loss sensor), data utilized to calculate grain yield may be collected (e.g., data describing the header width, the current ground speed or velocity of the combine harvester 10, and grain moisture data), the current GPS location of the combine harvester 10 may be determined (e.g., for constructing yield maps, such as the yield map 152 shown in FIG. 5), and so on. Finally, as noted above, the additional data inputs 018 can include operator input data entered via the operator interface 26 describing various crop attributes, such as operator input data identifying a currently-harvested grain type or operator input data directly specifying a kernel morphology classification of the currently-harvested grain.

Progressing to STEP 92 of the kernel-level grain monitoring process 86, the controller architecture 16 next calculates at least one APK parameter utilizing the data collected during STEP 90. As described throughout this document, such APK parameters can include any combination of: (i) APK volume, (ii) APK density, (iii) APK weight or mass, and (iv) APK morphology (size, shape, and angularity). Initially discussing APK volume, this parameter may be tracked by the controller architecture of the kernel-level grain monitoring system 12 via dimensional image analysis of the bulk grain sample images. Specifically, the controller architecture 16 may visually analyze the bulk grain sample images to identify the outlines of kernels within the bulk grain sample images; and then estimate and average certain dimensions (average length and diameter) of the detected kernels. Such average dimensions can then be utilized, potentially in combination with a known morphology or three dimensional shape of the kernels, to calculate an average per kernel volume of a single, average kernel within the bulk grain stream. Additional description of suitable image analysis techniques for monitoring APK volume utilizing the bulk grain sample images is described below in connection with FIG. 4.

The kernel-level grain monitoring system 12 may further monitor or track the APK density of the currently-harvested grain stream. In this case, the controller architecture 16 may: (i) determine a sample bulk density of the currently-generated grain stream; and (ii) calculate an APK density based, at least in part, on the sample bulk density of the grain stream and the APK volume. The controller architecture 16 can establish the sample bulk density of the grain stream based, at least in part, on data provided by the grain moisture sensor 64; e.g., indicative of the 1000 kernel weight or another weight parameter, as previously described. Further, in embodiments, the controller architecture 16 may further correct or compensate for air voiding when translating the bulk density measurement to a per kernel density parameter utilizing the kernel packing data 106. Specifically, while the APK volume can be utilized to estimate the number of kernels capable of fitting into a given volume of space or envelope, the APK volume does not, strictly considered, convey the manner in which such kernels will pack (colloquially, the "tightness" of kernel packing); and, therefore, does not directly indicate the fraction of such a spatial volume that, when packed by kernels from the grain stream, is occupied by air voids. Comparatively, the bulk density measurement (and the other "bulk" measurement described herein) inherently consider or taken into account the unoccupied (air void) space within a grain-packed spatial volume. Consequently, to compensate for this disparity between the APK parameters and the bulk measurements, the controller architecture 16 of the kernel-level grain monitoring system 12 may establish and utilize the above-described kernel packing data 106. As noted above, the kernel packing data 106 can be quantified as a percentage or fraction of a spatial volume occupied by grain mass or occupied by air voids; e.g., in one implementation, the kernel packing data 106 can be a percentage (ranging from, for example, 0.1% to 10%) estimating a cumulative volume of air voiding when the kernels of the currently-harvested grain are packed into a given spatial volume or envelope.

When utilized, the kernel packing data 106 can be determined by the controller architecture 16 based upon image analysis of the bulk grain sample images, as discussed below in connection with FIG. 4. Additionally or alternatively, the kernel packing data 106 may be determined based, at least in part, on a stored kernel packing indicator recalled from the database 84 stored in the memory 82 and corresponding to a grain type currently harvested utilizing the combine harvester 10. Accordingly, during STEP 92 of the of the kernel-level grain monitoring process 86, the controller architecture 16 may calculate the APK density utilizing the sample bulk density of the grain stream, the APK volume, and the kernel packing data 106. For example, in one approach, the controller architecture 16 may determine the bulk density measurement of the currently-harvested grain when packed into a given spatial volume, subtract the estimated air void volume from the total spatial volume of the bulk density measurement, and then calculate the APK density value by estimating the number of kernels capable of fitting into the corrected spatial volume corresponding to the bulk density measurement; e.g., in the case of a 1000 kernel weight, the number of kernels capable of fitting into a volumetric bushel (1.244 cubic feet or 0.035 cubic meters), less the estimated air void volume established utilizing the kernel packing data 106. Again, while the 1000 kernel weight is discussed herein as a common example, other grain density measurements can be employed in alternative embodiments in addition to or in lieu of the 1000 kernel weight.

Turning to APK weight (or mass), the controller architecture 16 can calculate this APK parameter as a function of the previously-established APK volume and a bulk grain weight (or mass) parameter. As will readily be appreciated, the APK mass can readily be calculated utilizing the APK weight (and, conversely, APK weight can readily be calculated utilizing the APK mass) as these parameters are directly proportional, noting that weight is the product of mass multiplied by the standard value of gravitational acceleration. In a manner similar to APK density, APK weight (or mass) can be readily determined utilizing a bulk weight (or mass) measurement in combination with the APK volume determined by the controller architecture 16, as described above. The kernel packing data 106 is also beneficially, although non-essentially considered by the controller architecture 16 in determining current values for the APK weight or APK mass. Generally, the controller architecture 16 may initially estimate the number of kernels capable of packing into a given volume of space based upon the APK volume and, perhaps, also considering the kernel packing data 106. After determining the kernel count within a given volume of space, the controller architecture 16 can estimate the APK weight or mass by dividing the bulk weight or mass measurement by the number of kernels contained within a spatial volume corresponding to the bulk weight or mass measurement. Again, such bulk weight or mass measurements may be presently calculated by conventional combine harvesters utilizing, for example, the strike plates 66 positioned adjacent the outlet end of the clean grain elevator 52, the grain tank load cells 68, or the other sensors 80.

Addressing lastly APK morphology, the controller architecture 16 can establish APK morphology classification of the bulk grain by visual analysis of the bulk grain sample images, whether performed onboard the combine harvester or offboard the combine harvester by a remote data source (e.g., a backend service) in wireless communication with the kernel-level grain monitoring system. Specifically, the controller architecture 16 may assign an APK morphology classification denoting an average kernel shape of kernels contained in the currently-harvested grain stream. Several examples of such morphology classes or types are shown in FIG. 3 and include linear, oblong, elliptic, ovate, spherical, and kidney shape classifications. Various other three dimensional kernel or seed shape categories can also be employed in addition to or in lieu of those presented in FIG. 3. Additionally, in embodiments, the controller architecture 16 may also assign a size or scale to the morphology class based, at least in part, upon dimensional analysis of the sample grain stream images. As an arbitrary example, a particular harvested grain may be assigned an APK morphology classification of a large oblong shape or a small spherical shape, with the controller architecture 16 potentially selecting from any practical number of size gradients. The APK morphology determination is thus similar, although distinct from the above-described APK calculation. Further description of example processes potentially employed by the controller architecture 16 to analyze the bulk grain sample images and determine an APK morphology classification, an APK volume, or both an APK morphology classification and an APK volume will now be described in connection with FIG. 4.

Figure 4:
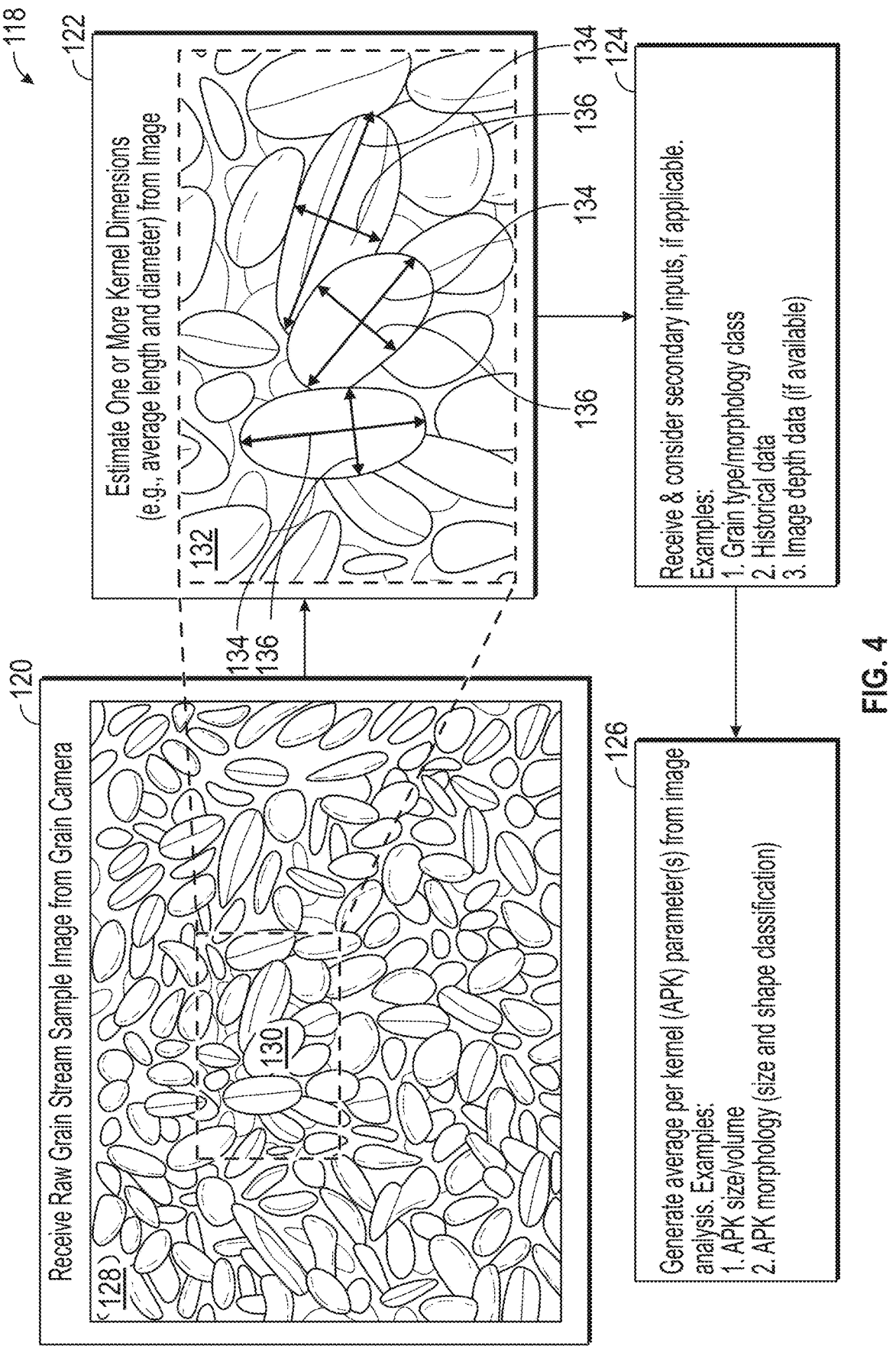
FIG. 4 schematically illustrates an example subprocess potentially conducted by the controller architecture of the kernel-level grain monitoring system to assess APK volume and/or APK morphology by dimensional image analysis of bulk grain sample images.

FIG. 4 schematically illustrates an example image analysis subprocess 118 potentially carried-out by the controller architecture 16 to assess APK volume, APK morphology, or both of these APK parameters via dimensional image analysis of bulk grain sample images, which are received from one or more cameras onboard the combine harvester 10; e.g., the grain camera 56 shown in FIGS. 1 and 2. The image analysis subprocess 118 includes four steps (STEPS 120, 122, 124, 126), which are performed in succession in the illustrated example. At STEP 120, the controller architecture 16 receives a raw camera image 128 of the grain stream from the grain camera 56. Next, at STEP 122, the controller architecture 16 may then processes the image (e.g., by increasing contrast and identifying regions of sharp contrast or other such visual "landmarks" to distinguish kernel outlines or perimeters) and thereby yield a processed image 132, a portion of which is shown in FIG. 4 for a magnified region 130 of the raw camera image 132. By identifying the outlines or perimeters of the kernels within the image, the controller architecture 16 may then identify the relevant dimensions of the kernels. The particular dimensions identified by the controller architecture 16 during STEP 122, and the manner in which the dimensions are applied to determine the APK volume, may vary depending upon the three dimensional shape of the kernels subject to analysis. For example, when the kernels are determined to possess generally spherical shapes on average (whether determined from operator input data, utilizing a look-up table correlating a current crop type to an average kernel shape, or determined based upon the above-described APK morphology), the controller architecture 16 may only determine the boundaries and outlines of visible kernels; assess a single dimension, such as the diameter (or perimeter) of the visually-sampled kernels; and then utilize the average diameter to calculate the volume of the spherical kernels as the APK volume utilizing well-known formulae for calculating spherical volume from a known diameter or perimeter value.

In other instances, the controller architecture 16 may determine the APK volume utilizing multiple estimated dimensions of the kernels depicted in the bulk grain sample images when, for example, the kernels have an oblong or irregular shape. In this latter regard, the controller architecture 16 may visually measure a length and a maximum width of each visually-analyzed kernel, as indicated in FIG. 4 by arrows 134, 136. Further, as indicated in FIG. 4 at STEP 124, this information may then be combined with the appropriate shape categorization or classification (here, an oval shape classification) to calculate the APK volume. Notably, in this case, the general orientation of the kernels depicted in the bulk sample grain images may become increasingly relevant. Considering this, the controller architecture 16 may apply filters or perform similar actions to restrict dimensional analysis to those kernels having length-wise orientations (that is, principally extend in a horizontal directions) in the analyzed imagery as opposed to kernels currently having increasingly upright orientations. For example, in embodiments, image analysis may be limited or restricted by the controller architecture 16 to those kernels identified as having a greater surface area revealed to the grain camera 56 and/or sufficiently matching the established kernel morphology shape, as seen from one or more selected sides of the kernel. This, in turn, may reduce the degree to which dimensional under-sizing errors result when, for example, some number of kernels having ovate shapes are positioned in upright orientations to reveal a generally circular surface area to the grain camera 56 (essentially, as seen when viewing the topside or bottomside of a given kernel). Accordingly, by restricting dimensional analysis to those kernels in which the ovular sides of the kernels are revealed, the accuracy with which APK volume and/or APK morphology is determined. A similar approach can also be employed for various other kernel morphology types, such as those shown in a boxed region 116 in STEP 92 of the example kernel-level grain monitoring process 86 set-forth in FIG. 3.

As further indicated in FIG. 4 at STEPS 124, 126, the above-described visual analysis of the bulk grain sample images can also consider depth data pertaining to the currently-harvested grain samples, when the combine harvester 10 is equipped with sensors capable of gathering such depth data. In this case, depth data may be utilized to establish the three dimensional geometry or topology of the kernels depicted in the bulk grain sample image to further increase the accuracy of the average per kernel (APK) volumetric calculations and/or kernel morphology assessments described above. Historical data can be also recalled from the memory 82 and blended with such two dimensional and three dimensional image data when available and so desired. For example, when utilized such historical data may be stored within the database 84 held within the memory 82 and may correlate morphological data (size and shape) of grain previously harvested in various field regions of a stored georeferenced map similar to a grain yield or grain loss map. Finally, the APK morphology of the kernels depicted in the bulk grain sample images can also be evaluated utilizing techniques similar to those described above. For example, an outline of the kernels may be determined and the general shape of the kernel outline may be compared prestored shapes or templates held within the database 84, each associated with a particular morphology classification. If depth data is available, a three dimensional mesh can be generated and similarly matched to three dimensional mesh templates within the database 84. In either instances, the controller architecture 16 can readily determine a APK morphology classification for the currently-harvested grain by image analysis of the bulk grain sample images. If such an APK morphology classification possess a size component, as in the case of a large linear APK morphology classification or a small kidney APK morphology classification, for example, the controller architecture 16 may determine this size component by dimensional analysis of the captured imagery utilizing processes or techniques analogous to those just described.

Returning to the kernel-level grain monitoring process 86 shown in FIG. 3, the controller architecture 16 next advances to STEP 94 and utilizes any or all of the above-described APK parameters to better inform (improve the accuracy of) topline harvesting metrics. For example, grain loss estimates can be improved by considering the APK mass parameter when grain loss is calculated utilizing the strike plate sensors 70 placed at certain locations in the combine harvester 10; e.g., by better estimating the mass of lost grain or by improving the strike count in more accurately distinguishing kernel impacts from other non-kernel (e.g., MOG) or broken kernel impacts. In this regard, during STEP 94, the controller architecture 16 may repeatedly estimate or track the APK mass of the currently-harvested grain; and monitor a grain loss parameter of the currently-harvested grain based, at least in part, on the estimated APK mass, impact data provided by the strike plate sensors 70, and any other relevant data inputs. Further, the determined APK weight can be scaled upwardly to a 1000 kernel weight value (or another multi-kernel weight parameter) by the controller architecture 16 in at least some implementations, with such an APK-based 1000 kernel weight utilized in place of the standardized 1000 kernel weight value conventionally relied upon by existing combine harvester systems in automating combine harvester setting adjustments. The accuracy and consistency with which grain losses are calculated and mapped may be improved as a result.

When monitored during the example kernel-level grain monitoring process 86, the APK morphology classification may also be considered by the controller architecture 16 to determine grain loss estimates with a greater degree of accuracy. Mass flow rate measurements can also be improved utilizing the APK parameters calculated by the kernel-level grain monitoring system 10 depending upon, for example, whether mass flow rate is tracked by measuring impacts against the strike plates 66 positioned at the outlet end of the clean gain elevator 52, utilizing the grain camera 56 (or another camera) to estimate the rate which grain is transported through the clean grain elevator 52, utilizing sensors indicating the clean grain elevator loading and speed to estimate mass flow rate, or utilizing another suitable technique. Grain yield estimates may also be improved utilizing the current or instantaneous values of the APK parameters, as appropriate. For example, in this latter regard, enhancements in the accuracy of calculating grain yield may result from more accurate mass flow rate estimations, which are commonly utilized to calculate grain yield in addition to combine header width, combine ground speed or velocity, and moisture data from the moisture sensor 64, as previously discussed. Similarly, test weight (the weight of the currently-harvested grain when tightly packed in a volumetric bushel) can be determined utilizing the APK parameters and, perhaps, kernel packing data, in the manner discussed above. Generally, then, embodiments of the kernel-level grain monitoring system 12 utilize disparate data inputs from the grain camera 56 and other onboard sensors (e.g., the moisture sensor 64) to improve the accuracy with which crucial crop information is calculated onboard the combine harvester 10.

As previously discussed, embodiments of the kernel-level grain monitoring system 12 may, but need not necessarily, perform further image analysis of the bulk grain sample images to assign the currently-harvested grain to a particular one of a plurality of predetermined APK morphology classifications or categories, as stored in the database 84. When so determined by the controller architecture 16, the APK morphology (size and shape) category or classification assigned to the kernels contained in the currently-harvested grain stream may also be usefully consumed as an input in calculations or algorithms to further enhance combine harvester performance and to provide other value-added functions, such as the creation of georeferenced data tools for subsequent analysis by relevant parties. In the latter regard, the APK morphology (size and shape) tracked by the controller architecture 16 and, perhaps, the APK weight parameters (which can be upscaled to one thousand kernel weight or another multi-kernel weight parameter) may be recorded along with GPS positions may enable seed producers and growers to improve product and services from an agronomical perspective. Further, as indicated in FIG. 3 by a graphic 95, the APK morphology (size and shape) may be utilized to more accurately infer or assess an angle of repose of the currently-harvested grain, which is also usefully known in carrying-out certain onboard calculations of the combine harvester 10. Generally, as the average kernel shape becomes increasingly rounded, the flowabilty of the bulk grain increases and piles of the bulk grain tend to flatten, thereby decreasing the angle of repose. Conversely, kernels having an increasingly oblong or irregular shapes tend to increase pile height and, therefore, have greater angles of repose (identified as angle $\alpha$ in the graphic 95). Once determined or estimated, the angle of repose may be utilized in fine tuning various calculations; e.g., the angle of repose may be utilized to more accurately assess an the amount or volume of grain piled onto the grain tank load cells 68, which, in turn, may improve mass flow sensor calibration techniques performed utilizing the load cell data. Stated differently, the controller architecture 16 may estimate an angle of repose of the currently-harvested grain based, at least in part, on the APK morphology classification; and then selectively calibrate the moisture sensor utilizing data generated by the load cells and the estimated angle of repose.

Figure 5:
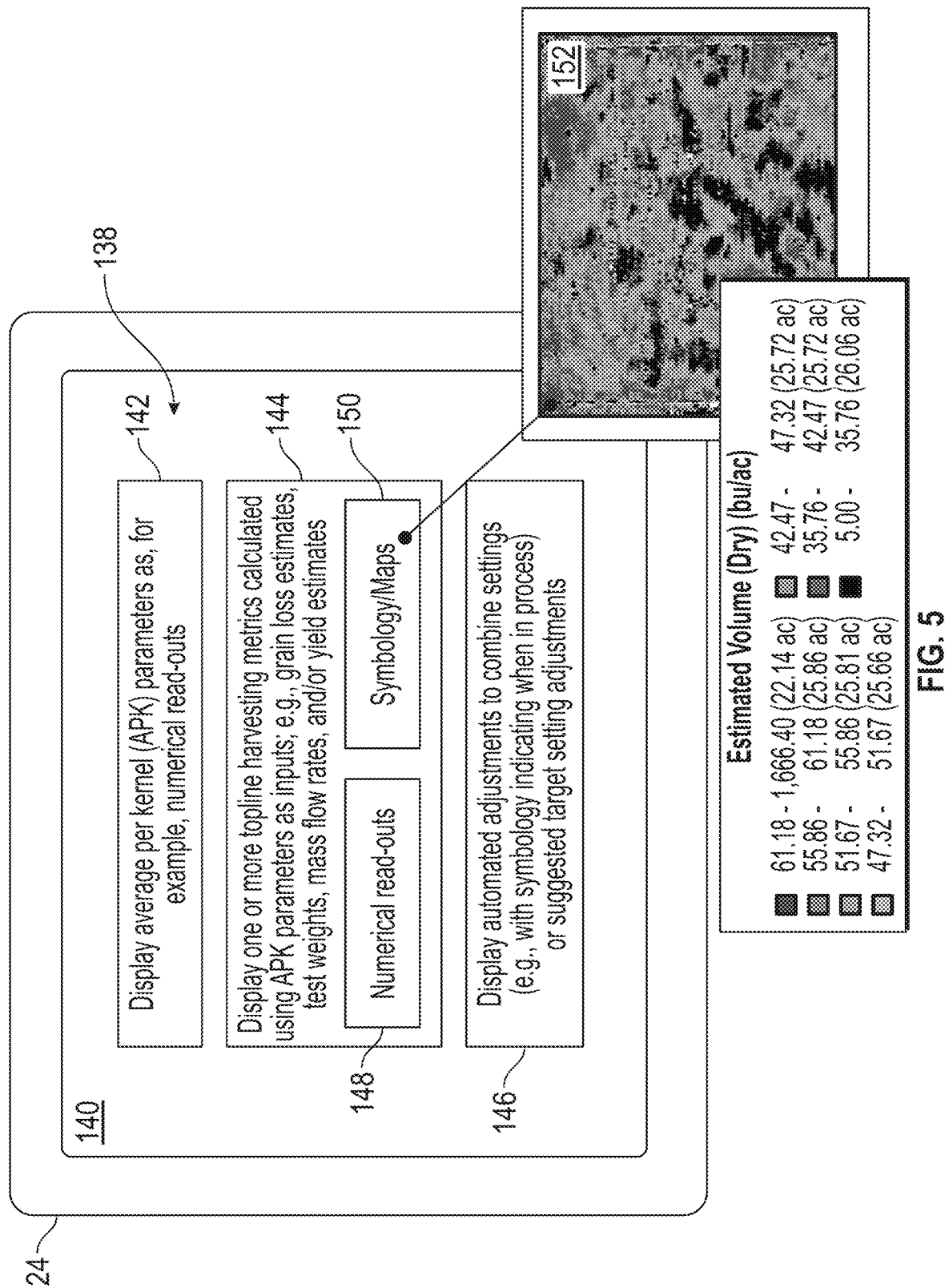
FIG. 5 is a screenshot of an example graphical user interface (GUI) screen suitably generated on a display device of the combine harvester by the kernel-level grain monitoring system and visually conveying any combination of the instantaneous values of the APK parameters, topline harvesting metrics consuming the APK parameters as inputs, and suggested combine setting adjustments determined utilizing the APK parameters.

Following STEP 94, the controller architecture 16 progresses to STEP 96 of the kernel-level grain monitoring process 86 and performs one or more actions utilizing the APK parameter(s) determined at STEP 92, the topline parameter(s) calculated at STEP 94, or a combination thereof. Such actions can include generating a GUI screen on the display device 24 enabling an operator to selectively view current or historical values of the APK parameters, as desired. This possibility is generically depicted in FIG. 5, which presents (in a generalized form) a GUI screen or page 138 generated on a display screen 140 of the display device 24 located in the cabin 22 of the combine harvester 10. As indicated by an upper bounded box 142, the controller architecture 16 can generate any number and type of numerical readouts or other visual indications conveying the current or instantaneous values of the APK parameters tracked by the kernel-level grain monitoring system 12. Similarly, at STEP 96 of the kernel-level grain monitoring process 86, the controller architecture 16 may visually express any topline harvesting metrics calculated by the controller architecture 16 utilizing the APK parameter(s), as genetically indicated in FIG. 5 within a boxed region 144. As indicated by box 148, the topline harvesting metrics can be expressed as numerical read-outs; e.g., numerical readouts of test weights, grain yield estimates, grain loss estimates, grain constituent or composition estimates, and/or mass flow rate estimates, to list but a few examples. Alternatively, as indicated within a boxed region 150, the topline harvesting parameters can be expressed in other graphic or symbology forms, such as yield maps, grain loss maps, and other agronomy information. An example of such a yield map 152, with different cross-hatching representing different color-coded region of the map 152 indicating different yield amounts, is shown in FIG. 5.

In embodiments, the controller architecture 16 may determine a target setting adjustment to the actuated harvesting component based on the tracked APK parameters, the topline harvesting metrics calculated utilizing the tracked APK parameters, or a combination thereof. Such information may be utilized to determine target adjustments to combine settings, which control the operation or positioning of the actuated harvesting components 76 described above in connection with FIG. 2. Further, the controller architecture 16 may generate imagery (e.g., a textual or symbol a visual notification) on the display device 24 prompt an operator to implement the determined target adjustments via appropriate visual cues. Additionally or alternatively, the controller architecture 16 may convey suggested adjustments to the combine harvester settings utilizing audible cues, such as by generation of annunciated messages or other audible notifications. As a still further possibility, the controller architecture 16 may automatically implement target setting adjustments to selected ones of the actuated harvesting components 76 onboard the combine harvester 10 when appropriate. In this latter regard, as an example, chafer adjustment, shoe adjustment, sieve adjustments, fan speed adjustments, the like may be determined and automatically implemented (that is, implemented without requiring operator input) by the controller architecture 16 of the kernel-level grain monitoring system 12 in at least some instances. This is indicated in FIG. 5 by a lower boxed region 146. As an example, relatively fine adjustments can be implemented to fan speeds to, for example, increase fan speeds in conjunction with increasing APK weight or size. Corresponding adjustments to the shoe, sieve, and/or chafer component positioning can also be automatically implemented in conjunction with fan speed adjustments in embodiments. When such automated adjustments are performed by the controller architecture 16, complementary graphics may be presented on the display screen 140 of the display device 24 and/or audible notifications may be generated to impart the operator with an awareness that such automated adjustments are being performed.

Following STEP 96, the controller architecture 16 determines whether the kernel-level grain monitoring process 86 should terminate (STEP 98) due to, for example, deactivation by an operator or cessation of crop harvesting by the combine harvester 10. If determining that the kernel-level grain monitoring process 86 should terminate, the controller architecture 16 advances to STEP 100 and terminates the process 86 accordingly. Otherwise, the controller architecture 16 returns to STEP 88 and performs a further iteration of the kernel-level grain monitoring process 86, as previously described. Such steps may be performed on a relatively rapid basis to allow the kernel-level grain monitoring system 12 to track the above-described APK parameters and perform the other actions described above (e.g., displaying selected APK parameters, displaying topline harvesting metrics calculated utilizing the APK parameters, and/or displaying or automatically implementing target setting adjustments determined utilizing the APK parameters) in highly responsive, real-time manner. This, in turn, may enhance the quality of information the kernel-level grain monitoring system 12 provides to combine harvester operators and may otherwise support optimization of combine harvester operation.

Enumerated Examples of the Kernel-Level Grain Monitoring System

The following examples of the kernel-level grain monitoring system are further provided and numbered for ease of reference.

1. In a first example embodiment, a kernel-level grain monitoring system includes a grain camera positioned to capture bulk grain sample images of a currently-harvested grain taken into and processed by a combine harvester, a moisture sensor configured to generate moisture sensor data indicative of a moisture level of the currently-harvested grain, and a display device having a display screen on which parameters pertaining to the currently-harvested grain are selectively presented. A controller architecture is coupled to the grain camera, to the moisture sensor, and to the display device. The controller architecture is configured to: (i) analyze the bulk grain sample images, as received from the grain camera, to determine an average per kernel (APK) volume representing an estimated volume of a single average kernel of the currently-harvested grain; (ii) repeatedly calculate one or more topline harvesting parameters based, at least in part, on the determined APK volume and the moisture sensor data; and (iii) selectively present the topline harvesting parameters on the display device for viewing by an operator of the combine harvester.

2. The kernel-level grain monitoring system of example 1, wherein the topline harvesting parameters include a kernel weight parameter.

3. The kernel-level grain monitoring system of example 2, wherein the kernel weight parameter includes a test weight specifying a weight of the currently-harvested grain when packed into a predetermined volume of space.

4. The kernel-level grain monitoring system of example 3, wherein the controller architecture is further configured to calculate the test weight utilizing a kernel packing data indicating a cumulative void space within the predetermined volume of space.

5. The kernel-level grain monitoring system of example 4, wherein the controller architecture is configured to determine the kernel packing data based, at least in part, on an image analysis assessment of cumulative void space within the bulk grain sample images.

6. The kernel-level grain monitoring system of example 4, further including an operator interface coupled to the controller architecture. The controller architecture is configured to determine the kernel packing data based, at least in part, on operator input data received via the operator interface.

7. The kernel-level grain monitoring system of example 4, further including a database storing a plurality of kernel packing data associated with different grain attributes. The controller architecture is configured to determine the kernel packing data by recalling a selected one of the plurality of kernel packing data corresponding to the currently-harvested grain.

8. The kernel-level grain monitoring system of example 1, further including at least one strike plate sensor coupled to the controller architecture and impacted by kernels of the currently-harvested grain when transported into a grain tank of the combine harvester. The controller architecture is coupled to the strike plate sensor and is configured to: (i) estimate an APK mass of the currently-harvested grain utilizing the APK volume and a bulk density parameter of the currently-harvested grain; and (ii) monitor a mass flow rate of the currently-harvested grain based, at least in part, on the estimated APK mass and impact data provided by the strike plate sensor.

9. The kernel-level grain monitoring system of example 8, wherein the topline harvesting parameters include a grain yield parameter calculated utilizing the mass flow rate as an input.

10. The kernel-level grain monitoring system of example 1, wherein the controller architecture is configured to further analyze the bulk grain sample images, as received from the grain camera, to determine an APK morphology classification indicating a kernel size and shape category of the currently-harvested grain.

11. The kernel-level grain monitoring system of example 10, further including load cells located in a grain tank of the combine harvester. The controller architecture is further configured to: (i) estimate an angle of repose of the currently-harvested grain based, at least in part, on the APK morphology classification; and (ii) selectively calibrate the moisture sensor utilizing data generated by the load cells and the estimated angle of repose.

12. The kernel-level grain monitoring system of example 1, further including strike plate sensors coupled to the controller architecture and impacted by kernels of the currently-harvested grain when ejected from the combine harvester. The controller architecture is coupled to the strike plate sensors and is configured to: (i) estimate an APK mass of the currently-harvested grain utilizing the APK volume and a bulk density parameter of the currently-harvested grain; and (ii) monitor a grain loss parameter of the currently-harvested grain based, at least in part, on the estimated APK mass and impact data provided by the strike plate sensors.

13. The kernel-level grain monitoring system of example 1, further including an actuated harvesting component onboard the combine harvester and coupled to the controller architecture. The controller architecture is further configured to determine a target setting adjustment to the actuated harvesting component based, at least in part, on a parameter calculated utilizing the APK volume. Additionally, the controller architecture performs at least one of the following actions: (i) generating graphics on the display device visually prompting an operator to implement the target setting adjustment to the actuated harvesting component, or (ii) automatically implementing the target setting adjustment to the actuated harvesting component.

14. The kernel-level grain monitoring system of example 13, wherein the parameter calculated utilizing the APK volume includes at least one of an APK weight, an APK mass, and an APK density, which the target setting adjustment entails a fan speed adjustment.

15. In further embodiments, the kernel-level grain monitoring system includes a grain camera positioned to capture bulk grain sample images of a currently-harvested grain taken into and processed by the combine harvester, a moisture sensor configured to generate moisture sensor data indicative of a moisture level of the currently-harvested grain, a display device having a display screen on which parameters pertaining to the currently-harvested grain are selectively presented. A controller architecture coupled to the grain camera, to the moisture sensor, and to the display device. The controller architecture is configured to analyze the bulk grain sample images, as received from the grain camera, to determine an average per kernel (APK) parameter; and determine a target setting adjustment to an actuated harvesting component of the combine harvester based, at least in part, on the APK parameter. Additionally, the controller architecture performs at least one of the following actions: (i) generating a notification, such as a visual and/or audible notification, prompting an operator to implement the target setting adjustment; and (ii) controlling the actuated harvesting component to automatically implement the target setting adjustment.

CONCLUSION

There has thus been provided embodiments of a kernel-level grain monitoring system for usage onboard combine harvesters. Embodiments of the kernel-level grain monitoring system utilize bulk grain sample images obtained from at least one grain camera to calculate one or more APK parameters pertaining a bulk grain stream generated by a combine harvester. The instantaneous values of one or more of the APK parameters, such as APK volume (size), APK weight or mass, APK density, and/or APK morphology, can be directly displayed to an operator of the combine harvester in embodiments. Additionally or alternatively, the APK parameters may be utilized to calculated topline harvesting metrics, including any combination of mass flow rates, grain yields, test weights, grain losses, and other parameters, with higher degrees of accuracy and consistency. The topline harvesting metrics can then be displayed to operators for consideration in determining an optimal manner in which to pilot a combine harvester under a given set of circumstances, utilized to calibrate sensors (e.g., the mass flow rate sensor) onboard the combine harvester, or stored in memory for subsequent reference or usage in compiling agronomical data tools, such as yield and grain loss maps. In certain embodiments, the APK parameters and/or the topline harvesting metrics calculated utilizing the APK parameters may be leveraged to determine target adjustments to combine harvester settings, with the target setting adjustments then conveyed (e.g., visually presented or audibly communicated) to combine harvester operators or automatically implemented by the kernel-level grain monitoring system. Advantageously, such APK parameters can be calculated by combining different sensor inputs provided by sensors (including the grain camera and moisture sensor) commonly deployed onboard existing combine harvesters. Consequently, in many instances, the kernel-level grain monitoring system can be implemented principally through software to streamline user adoption and lower implementation costs. Generally, then, embodiments of the kernel-level grain monitoring system avail operators and automated systems of novel and higher quality information to enhance various aspects of combine harvester operation.

As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Explicitly referenced embodiments herein were chosen and described in order to best explain the principles of the disclosure and their practical application, and to enable others of ordinary skill in the art to understand the disclosure and recognize many alternatives, modifications, and variations on the described example(s). Accordingly, various embodiments and implementations other than those explicitly described are within the scope of the following claims.

What is claimed is:

1. A kernel-level grain monitoring system utilized onboard a combine harvester, the kernel-level grain monitoring system comprising:

a grain camera positioned to capture bulk grain sample images of a currently-harvested grain taken into and processed by the combine harvester; and a strike plate sensor configured to be impacted by kernels of the currently-harvested grain;

a controller architecture coupled to the grain camera and to the strike plate sensor, the controller architecture configured to:

analyze the bulk grain sample images, as received from the grain camera, to determine an average per kernel (APK) volume representing an estimated volume of a single average kernel of the currently-harvested grain;

estimate an APK mass of the currently-harvested grain utilizing the APK volume;

monitor a mass flow rate of the currently-harvested grain based, at least in part, on the estimated APK mass and impact data provided by the strike plate sensor;

calculate one or more topline harvesting parameters based, at least in part, on the determined APK volume; and output the topline harvesting parameters to an operator of the combine harvester.

2. The kernel-level grain monitoring system of claim 1, wherein the combine harvester includes a grain tank; and wherein the strike plate sensor is configured to sense impacts of kernels of the currently-harvested grain when the kernels are transported into the grain tank.

3. The kernel-level grain monitoring system of claim 1, wherein the strike plate sensor is configured to sense impacts of kernels of the currently-harvested grain when the kernels are ejected from the combine harvester.

4. The kernel-level grain monitoring system of claim 1, wherein the controller architecture is configured to estimate the APK mass of the currently-harvested grain utilizing the APK volume and a bulk density parameter of the currently-harvested grain.

5. The kernel-level grain monitoring system of claim 1, wherein the topline harvesting parameters comprise a grain yield parameter calculated utilizing the mass flow rate as an input.

6. The kernel-level grain monitoring system of claim 1, further comprising a moisture sensor configured to generate moisture sensor data indicative of a moisture level of the currently-harvested grain; and wherein the controller architecture is configured to calculate the one or more topline harvesting parameters based, at least in part, on the determined APK volume and the moisture sensor data.

7. The kernel-level grain monitoring system of claim 1, further comprising a display device that includes a display screen on which parameters pertaining to the currently-harvested grain are selectively presented;

wherein the controller architecture is configured to selectively present the topline harvesting parameters on the display device for viewing by an operator of the combine harvester.

8. A kernel-level grain monitoring system utilized onboard a combine harvester having an actuated harvesting component, the kernel-level grain monitoring system comprising:

a grain camera positioned to capture bulk grain sample images of a currently-harvested grain taken into and processed by the combine harvester;

a strike plate sensor configured to be impacted by kernels of the currently-harvested grain; and a controller architecture coupled to the grain camera and the strike plate sensor, the controller architecture configured to:

analyze the bulk grain sample images, as received from the grain camera, to determine an average per kernel (APK) parameter;

monitor a grain flow rate of the combine harvester based, at least in part, on the APK parameter and impact data provided by the strike plate sensor; and based on the APK parameter, either generate a notification to an operator to adjust the actuated harvesting component or automatically adjust the actuated harvesting component.

9. The kernel-level grain monitoring system of claim 8, wherein the combine harvester has a grain tank; and wherein the strike plate sensor is configured to sense impacts of kernels of the currently-harvested grain when transported into the grain tank.

10. The kernel-level grain monitoring system of claim 8, wherein the strike plate sensor is configured to sense impacts of kernels of the currently-harvested grain when ejected from the combine harvester.

11. The kernel-level grain monitoring system of claim 8, wherein the APK parameter comprises an APK volume.

12. The kernel-level grain monitoring system of claim 11, wherein the controller architecture is configured to estimate an APK mass of the currently-harvested grain utilizing the APK volume and a bulk density parameter of the currently-harvested grain.

13. The kernel-level grain monitoring system of claim 8, further comprising a moisture sensor configured to generate moisture sensor data indicative of a moisture level of the currently-harvested grain; and wherein the controller architecture is configured to calculate one or more topline harvesting parameters based, at least in part, on the APK volume and the moisture sensor data.

14. The kernel-level grain monitoring system of claim 8, further comprising a display device that includes a display screen on which parameters pertaining to the currently-harvested grain are selectively presented;

wherein the controller architecture is configured to selectively present the topline harvesting parameters on the display device for viewing by an operator of the combine harvester.

15. A kernel-level grain monitoring system utilized onboard a combine harvester, the kernel-level grain monitoring system comprising:

a grain camera positioned to capture bulk grain sample images of a currently-harvested grain taken into and processed by the combine harvester;

a display device having a display screen on which parameters pertaining to the currently-harvested grain are selectively presented; and a strike plate sensor configured to be impacted by kernels of the currently-harvested grain;

a controller architecture coupled to the grain camera, to the strike plate sensor, and to the display device, the controller architecture configured to:

analyze the bulk grain sample images, as received from the grain camera, to determine an average per kernel (APK) volume representing an estimated volume of a single average kernel of the currently-harvested grain;

estimate an APK mass of the currently-harvested grain utilizing the APK volume;

monitor a mass flow rate of the currently-harvested grain based, at least in part, on the estimated APK mass and impact data provided by the strike plate sensor;

calculate one or more topline harvesting parameters based, at least in part, on the determined APK volume; and selectively present the topline harvesting parameters on the display device for viewing by an operator of the combine harvester.

16. The kernel-level grain monitoring system of claim 15, wherein the combine harvester includes a grain tank; and wherein the strike plate sensor is configured to sense impacts of kernels of the currently-harvested grain when transported into the grain tank.

17. The kernel-level grain monitoring system of claim 15, wherein the strike plate sensor is configured to sense impacts of kernels of the currently-harvested grain when ejected from the combine harvester.

18. The kernel-level grain monitoring system of claim 15, wherein the controller architecture is configured to estimate the APK mass of the currently-harvested grain utilizing the APK volume and a bulk density parameter of the currently-harvested grain.

19. The kernel-level grain monitoring system of claim 15, wherein the topline harvesting parameters comprise a grain yield parameter calculated utilizing the mass flow rate as an input.

20. The kernel-level grain monitoring system of claim 15, further comprising a moisture sensor configured to generate moisture sensor data indicative of a moisture level of the currently-harvested grain; and wherein the controller architecture is configured to calculate the one or more topline harvesting parameters based, at least in part, on the determined APK volume and the moisture sensor data.

* * * * *